(12) United States Patent
Cobb et al.

(10) Patent No.: US 11,768,194 B2
(45) Date of Patent: Sep. 26, 2023

(54) SYSTEM AND METHOD FOR IMAGING AND ILLUMINATION FOR CELL CONFLUENCE MEASUREMENT

(71) Applicant: CORNING INCORPORATED, Corning, NY (US)

(72) Inventors: Joshua Monroe Cobb, Victor, NY (US); Gregory Roger Martin, Acton, ME (US); Robert Raymond Raczkowski, Corning, NY (US); Mark Christian Sanson, Macedon, NY (US); Horst Schreiber, Livonia, NY (US); Todd Michael Upton, Eliot, ME (US)

(73) Assignee: CORNING INCORPORATED, Corning, NY (US)

( * ) Notice: Subject to any disclaimer, the term of this patent is extended or adjusted under 35 U.S.C. 154(b) by 0 days.

(21) Appl. No.: 17/564,465

(22) Filed: Dec. 29, 2021

(65) Prior Publication Data
US 2022/0120729 A1     Apr. 21, 2022

Related U.S. Application Data

(63) Continuation of application No. 16/797,378, filed on Feb. 21, 2020, now abandoned, which is a
(Continued)

(51) Int. Cl.
*C12M 1/32*     (2006.01)
*C12M 1/34*     (2006.01)
(Continued)

(52) U.S. Cl.
CPC ......... *G01N 33/4833* (2013.01); *C12M 23/12* (2013.01); *C12M 41/46* (2013.01);
(Continued)

(58) Field of Classification Search
CPC ....... C12M 23/12; C12M 41/46; G01N 21/55; G01N 33/4833; G01N 33/5005;
(Continued)

(56) References Cited

U.S. PATENT DOCUMENTS

| 5,470,746 A | 11/1995 | Kim |
| 5,715,933 A * | 2/1998 | Monahan ................. B44D 3/02 206/518 |

(Continued)

FOREIGN PATENT DOCUMENTS

| DE | 202009010255 U1 | 10/2009 |
| DE | 102016217250 A1 | 3/2018 |

(Continued)

OTHER PUBLICATIONS

Cobb et al., U.S. Appl. No. 16/690,583, titled "Compact Optical Imaging System for Cell Culture Monitoring," filed Nov. 21, 2019.
(Continued)

*Primary Examiner* — Yubin Hung
(74) *Attorney, Agent, or Firm* — Chandra J. Duncan

(57) ABSTRACT

A cell monitoring plate comprises a flat surface on which multiple cell culturing vessels may be stacked. The flats surface has multiple optical imaging systems embedded therein to fully image a cell culture vessels stacked on the plate. Each one of the multiple optical imaging systems provides both illumination and imaging through a single aperture in the surface of the monitoring plate.

16 Claims, 14 Drawing Sheets

Related U.S. Application Data continuation of application No. PCT/US2019/063712, filed on Nov. 27, 2019.

(60) Provisional application No. 62/773,899, filed on Nov. 30, 2018.

(51) Int. Cl.
| | |
|---|---|
| *G02B 21/00* | (2006.01) |
| *G02B 21/04* | (2006.01) |
| *G02B 21/36* | (2006.01) |
| *G01N 21/55* | (2014.01) |
| *G01N 33/483* | (2006.01) |
| *G01N 33/50* | (2006.01) |

(52) U.S. Cl.
CPC .......... *G01N 21/55* (2013.01); *G01N 33/5005* (2013.01); *G02B 21/361* (2013.01); *G02B 21/002* (2013.01); *G02B 21/04* (2013.01); *G02B 21/36* (2013.01)

(58) Field of Classification Search
CPC ...... G02B 21/002; G02B 21/04; G02B 21/36; G02B 21/361
See application file for complete search history.

(56) References Cited

U.S. PATENT DOCUMENTS

| | | | |
|---|---|---|---|
| 5,858,769 A | 1/1999 | Diguiseppi et al. | |
| 5,926,311 A | 7/1999 | Cobb et al. | |
| 6,795,239 B2* | 9/2004 | Tandler .................. | G02B 21/06 359/368 |
| 7,796,328 B2 | 9/2010 | Wolleschensky | |
| 10,501,718 B2 | 12/2019 | Matsushita et al. | |
| 2003/0205681 A1* | 11/2003 | Modlin ................ | G01N 21/648 250/459.1 |
| 2003/0231537 A1 | 12/2003 | Stark | |
| 2005/0219526 A1 | 10/2005 | Peng | |
| 2006/0166305 A1* | 7/2006 | Jiang .................... | G01N 21/253 435/29 |
| 2008/0068710 A1 | 3/2008 | Wolleschensky | |
| 2008/0082468 A1* | 4/2008 | Long .................... | G06V 10/764 706/12 |
| 2008/0266545 A1 | 10/2008 | Hansen | |
| 2010/0035337 A1 | 2/2010 | Bahnemann et al. | |
| 2013/0038727 A1* | 2/2013 | Clark .................... | C12M 41/46 348/143 |
| 2013/0176897 A1 | 7/2013 | Wang et al. | |
| 2015/0087240 A1* | 3/2015 | Loewke ................. | G06T 7/143 455/67.11 |
| 2015/0329813 A1 | 11/2015 | Martin et al. | |
| 2016/0299069 A1 | 10/2016 | Yu et al. | |
| 2017/0044481 A1* | 2/2017 | Kawano .................. | H04N 1/00 |
| 2017/0145370 A1 | 5/2017 | Kato et al. | |
| 2017/0257538 A1* | 9/2017 | Kokubo ................. | G06V 20/693 |
| 2018/0045944 A1* | 2/2018 | Suzuki ................. | G02B 21/367 |
| 2018/0291328 A1 | 10/2018 | Sasaki et al. | |
| 2019/0094511 A1* | 3/2019 | Chan ..................... | G02B 21/16 |
| 2019/0114465 A1 | 4/2019 | Shibata et al. | |
| 2019/0180080 A1 | 6/2019 | Iga et al. | |
| 2019/0376020 A1 | 12/2019 | Bickham et al. | |
| 2019/0376897 A1* | 12/2019 | Smith .................. | G01N 21/253 |
| 2020/0002661 A1 | 1/2020 | Kesyou et al. | |
| 2020/0064610 A1 | 2/2020 | Echigo | |
| 2020/0082222 A1* | 3/2020 | Cohen .................... | G06N 3/084 |
| 2020/0217782 A1 | 7/2020 | Fukushima et al. | |
| 2020/0318058 A1 | 10/2020 | Mochizuki et al. | |
| 2020/0379231 A1* | 12/2020 | Dohi ..................... | C12M 23/14 |

FOREIGN PATENT DOCUMENTS

| | | |
|---|---|---|
| EP | 3009500 A1 | 4/2016 |
| EP | 3211469 A1 | 8/2017 |
| JP | 2018-102228 A | 7/2018 |
| WO | 2011/090792 A1 | 7/2011 |
| WO | 2018/136797 A1 | 7/2018 |

OTHER PUBLICATIONS

International Search Report and Writien Opinion of the European International Searching Authority; PCT/US2019/063712; dated Feb. 27, 20; 13 Pgs.

International Search Report and Written Opinion of the International Searching Authority; PCT/US2019/063712; dated Feb. 27, 2020; 11 Pages; European Patent Office.

International Search Report and Written Opinion of the International Searching Authority; PCT/US2019/062137; dated Jun. 25, 2020; 18 Pages; European Patent Office.

Invitation to Pay Additional Fees and Partial Search Report of the European International Searching Authority; PCT/US2019/062137; dated Mar. 2, 2020; 17 Pgs.

Invitation to Pay Additional Fees of the International Searching Authority PCT/US2019/062137; dated Mar. 2, 2020; 17 Pages; European Patent Office.

* cited by examiner

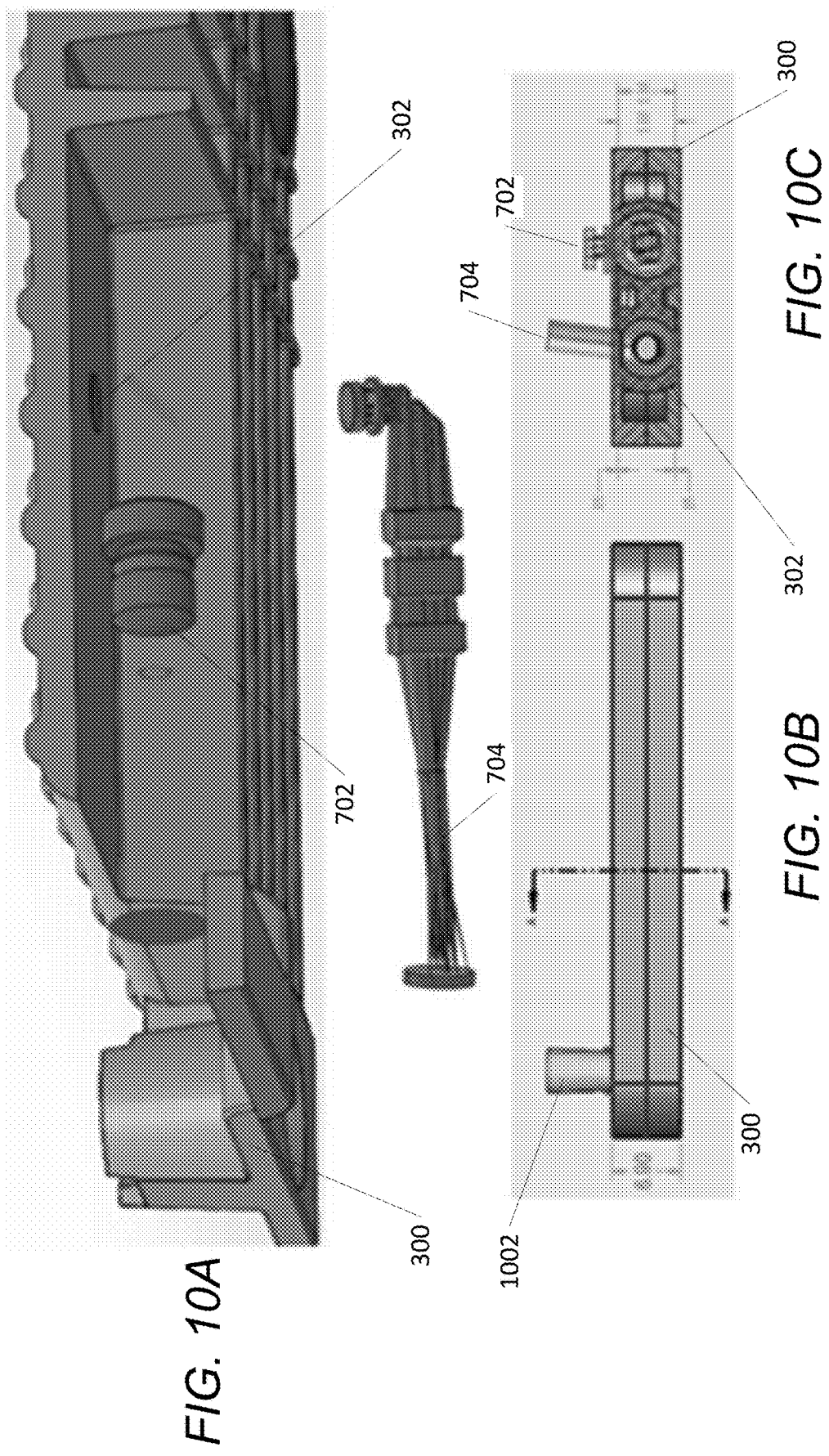

SYSTEM AND METHOD FOR IMAGING AND ILLUMINATION FOR CELL CONFLUENCE MEASUREMENT

RELATED APPLICATIONS

This application is a continuation of U.S. patent application Ser. No. 16/797,378 filed on Feb. 21, 2020, which is a continuation of International Application No. PCT/US2019/063712 filed on Nov. 27, 2019, which claims the benefit of priority under 35 U.S.C § 120 of U.S. Provisional Application Ser. No. 62/773,899 filed on Nov. 30, 2018, both applications being incorporated herein by reference.

FIELD OF THE INVENTION

This invention pertains to the field of laboratory work, and, in particular, to the equipment and methods used in a laboratory environment for imaging of microscopic structures such as cells. More particularly, the present disclosure relates to systems and methods for measurement of cell culture confluence.

BACKGROUND OF THE INVENTION

Cell culture is an indispensable tool that has found many important and valuable applications in a wide range of areas such as drug screening, toxicity testing, genetic engineering, therapeutic protein and vaccine production. In general, mammalian cell lines are cultured in an incubator, where it is beneficial to closely monitor and control temperature, humidity and $CO_2$ content. During the cell culture processes, the cells seeded in a culture vessel filled with culture media must be monitored as they grow before being processed in downstream processes.

For example, cell confluency of cell culture may be monitored. Generally, cells are subcultured or passaged when they reach 80%-90% confluency because cells could lose their proliferating and gene expression phenotype when they become overgrown. In addition to cell confluency, a wide range of other important applications such as cell migration tracking, cell density measurement, and total cell number estimation also require frequent observation.

To visualize confluency, a bench top light microscope is typically used. Cell culture vessels containing both cells and cell culture media are taken out of the cell incubator and placed on a specimen stage of a light microscope. Researchers observe the cells in a bright field mode through the ocular lens (eyepiece) of the microscope. Cell confluency is often measured by counting cells, which can be a tedious and error-prone process.

The method of observation with a bench top light microscope has several major drawbacks. For example, researchers have to frequently manually take cell culture vessels out of the cell incubator. This procedure may interfere with the cell culture process. When cell culture vessels are removed from the cell incubator, the cells experience an environment change including temperature, atmosphere and humidity. Furthermore, there exists potential that the cell culture gets contaminated due to frequent contact of cell culture vessels with incompletely sterilized labware outside of the cell incubator. The contamination of cell cultures with microorganisms (bacteria, fungi, yeast, etc.) can change the biochemical and biophysical behaviors of cells, or even cause the death of cells.

Thus, there is a desire and need to monitor cells without having to physically move the cell culture vessels from the incubator environment to a microscope. One significant problem is that the illumination required for viewing these cells with high contrast must come from behind the cells, that is, a back illumination that transmits through the cells and then enters the objective lens of the microscope. This becomes challenging if the optical imaging system and the illumination system are physically located in different places in the stack. It would be very beneficial to have the imaging and illumination channels in the same area of the stack to make modifications to the tray stacks and alignment between the channels easier.

SUMMARY OF THE INVENTION

Disclosed herein is a system and method for imaging cells in trays with illumination and imaging systems that sit side-by-side but still allow for back illumination of the cells. The imaging and illumination system is compact and functional and can be used with cell growth trays.

The invention includes at least one transparent tray for growing living cells, a second tray stacked on top of the first tray, an imaging system for forming an image of an area in the tray where cells are growing, an illumination system for back illuminating the cells in transmission. The imaging system includes a lens system, a telecentric aperture stop, and an image sensor. The illumination system includes a light source for generating a light within a spectral band and a lens for creating a collimated image of the light source, wherein the collimated image of the source passes through the surface of the tray that the cells are growing on at an oblique angle and reflects off the second tray surface to back illuminate the cells on the first tray surface and wherein this back illuminated light then enters the imaging system and the image of the source is re-imaged by the imaging system lens into the telecentric stop and the image of the cells is created on the image sensor.

It is an object of this invention that the optical axis of the illumination system is reflected into the optical axis of the imaging system by a tray surface above the object tray. This allows the illumination system to be next to the imaging system and yet still illuminate the object cells from behind. This configuration requires the plane of the cells to be at an oblique angle to the optical axis of both the illumination and the imaging systems. Thus, the image plane created by the imaging system lens is tilted at an angle to the optical axis. This creates a focus shift across the field of view unless the image sensor is tilted to compensate this by satisfying the Scheimpflug condition.

Integrating the invention into a stand-alone monitoring plate can allow the use of the system with industry standard cell culturing vessels. The invention has an advantage because the illumination system and the imaging system are next to each other and, as such, can be installed as a monolithic apparatus. They can be pre-aligned to each other and take up minimal space in the cell growth trays. Any space taken up by a camera system is space that cannot be used for cell growth. This minimizes the space and creates an image of the cells by rear illumination.

BRIEF DESCRIPTION OF THE DRAWINGS

FIG. 10, View (A) shows a cut-away view of the monitoring plate showing positioning of one or the multiple optical imaging systems. View (B) shows a side view of the monitoring plate, showing the relatively thin aspect ratio. View (C) is a top view of one aperture in the top surface of the monitoring plate, showing the imaging and illumination components of a single optical imaging system sharing the aperture.

DEFINITIONS

Figure 1:
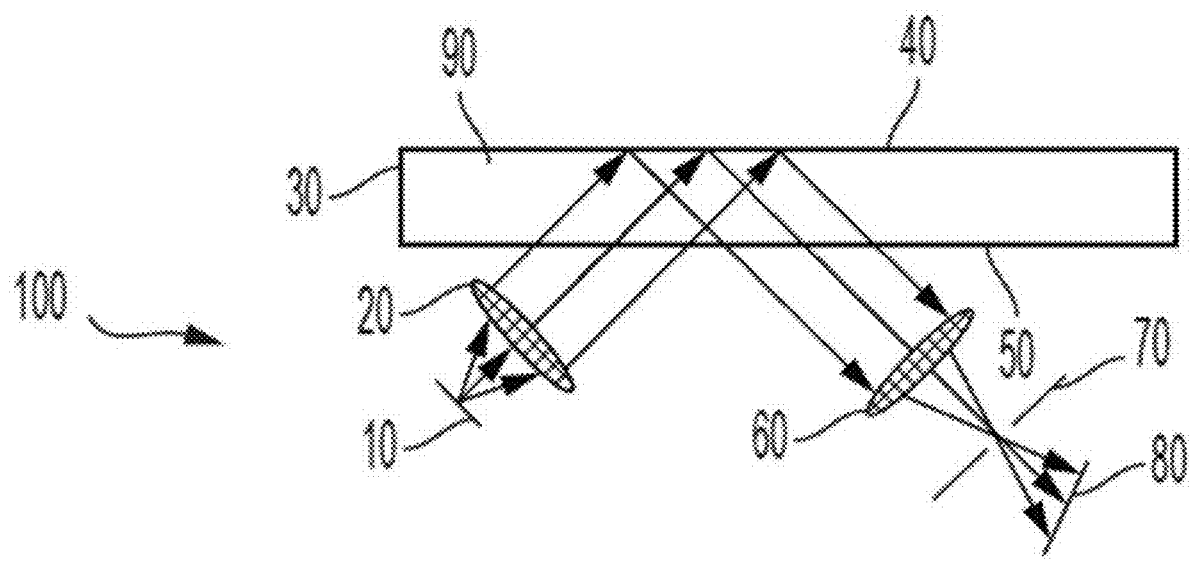
FIG. 1 schematically illustrates a detector/illumination source for a single cell culture plate.

The terms "confluence" and "confluency", as used herein, refer to the proportion of a cell culture substrate surface occupied by cells.

As used herein, "have," "having," "include," "including," "comprise," "comprising" or the like are used in their open-ended sense, and generally mean "including, but not limited to."

The singular forms "a," "an" and "the" include plural referents unless the context clearly dictates otherwise. The endpoints of all ranges reciting the same characteristic are independently combinable and inclusive of the recited endpoint. All references are incorporated herein by reference.

The terms "top", "bottom", "side", "upper", "lower", "above", "below" and the like are used herein for descriptive purposes and not necessarily for describing permanent relative positions. It should be understood that the terms so used are interchangeable under appropriate circumstances such that embodiments of the present disclosure are, for example, capable of operation in other orientations than those illustrated or otherwise described herein.

DETAILED DESCRIPTION

Reference will now be made in detail to the present embodiment(s), an example(s) of which is/are illustrated in the accompanying drawings. Whenever possible, the same reference numerals will be used throughout the drawings to refer to the same or like parts.

All scientific and technical terms used herein have meanings commonly used in the art unless otherwise specified. Any definitions provided herein are to facilitate understanding of certain terms used frequently herein and are not meant to limit the scope of the present disclosure.

The present disclosure is described below, at first generally, then in detail on the basis of several exemplary embodiments. The features shown in combination with one another in the individual exemplary embodiments do not all have to be realized. In particular, individual features may also be omitted or combined in some other way with other features shown of the same exemplary embodiment or else of other exemplary embodiments.

The invention comprises an illumination and imaging system to view cells growing on a flat tray bottom. When viewing an object that is transparent, it can be difficult to see any contrast in the edges of the cell. One method that works well is to illuminate the cells from behind and direct the illumination source to enter and underfill the entrance pupil of the objective lens of the imaging system.

Embodiments of this invention provide the benefit of positioning the imaging and illumination channels on the same side of the cells being imaged. Thus, the imaging and illumination channels can be located in the same area of the cell culture stack, making modifications to the tray stacks and alignment between the channels easier. In addition, embodiments of this invention offer compact imaging solutions that allow cell culture vessels to remain in-place for imaging, eliminating the need to relocate a cell culture vessel from an incubator environment to an imaging platform. Such relocation of the vessel is not desirable as it can disturb the cells, change the environmental conditions of the cells, thereby negatively impact the resulting cell culture.

Embodiments of the present disclosure relate to a compact optical imaging system for cell culture monitoring built into a monitoring plate on which multiple cell culture trays may be stacked. The monitoring plate includes a plurality of detectors and illumination sources. A collimating lens is positioned between a surface of a cell culture vessel and the illumination source, wherein the illumination source is configured to emit light at an angle oblique to the surface of the cell culture vessel. The detector has a related lens positioned between the surface of the cell culture vessel and the detector, wherein the lens focuses light to the detector through an aperture stop, and wherein the detector is configured to receive light exiting the surface of the cell culture vessel at an angle oblique to the surface.

The system is configured to be operated in bright field mode, which allows for various aspects of cell culture health to be determined through image analysis of a bright field image. Additionally, systems as described herein have a small footprint that permits the system to be integrated into, or removably associated with, a cell culture vessel in a way that allows for continuous monitoring of cell culture status using a bright field mode.

FIG. 1 schematically illustrates one of the plurality of detector/illumination source from a monitoring plate. It should be appreciated that the schematic illustration of FIG. 1 is not drawn to scale. As shown, the compact optical imaging system 100 includes an illumination source 10 and a collimating lens 20. The illumination source 10 is oriented to emit light that is collimated by the collimating lens 20 and directed toward a first surface 50 of a cell culture vessel 30. The illumination source 10 may be, for example but not limited to, a light emitting diode (LED) or an array of LEDs. Alternatively, the illumination source 10 may be a non-LED light source, such as an incandescent, compact fluorescent (CFL), halogen, or other source configured to produce and emit a beam of light. The illumination source 10 may produce a white light or a colored light of any wavelength or combination of wavelengths in the visible spectrum.

As further shown in FIG. 1, the optical imaging system 100 includes a detector 80. The detector 80 includes an image sensor for detecting light impinging on the image sensor and converting the light into an electrical signal. The image sensor may be a charge-coupled device (CCD) sensor, a complementary metal oxide semiconductor (CMOS) sensor, or any other type of sensor that is capable of converting light into an electrical signal. Alternatively, the detector 80 may simply include a CCD, CMOS, or other image sensor. The system 100 further includes a lens 60 for collecting light and an aperture stop 70 disposed between the first surface 50 of the cell culture vessel 30 and the detector 80, wherein the lens 60 collects light and focuses the light through the aperture stop 70 and onto the detector 80.

According to embodiments of the present disclosure, the illumination source 10, collimating lens 20, and any other optical components in the path of the light emitted from the illumination source 10 are positioned to transmit the light such that the direction of the light beam as it enters the cell culture vessel 100 is at an angle oblique to the first surface 50. Similarly, the detector 80 is positioned at an angle to receive light exiting the first surface 50 of the cell culture vessel 100 at an angle that is oblique to the surface 50 (i.e., neither parallel to or at a right angle to surface 50). In operation, a light beam is emitted from the illumination source 10 in the direction of the first surface 50 of the cell culture vessel 30, wherein the first surface 50 contains live cells to be imaged. The light beam travels into and through a cell culture vessel 90 of the cell culture vessel 30, contacts a second surface 40 of the cell culture vessel 30 positioned on an opposite side of the cell culture vessel 90, and is redirected at an angle in the direction of the detector 80. After being redirected, the light passes through cells on the first surface 50 of the cell culture vessel 30 before being focused by lens 60 to the aperture stop 70. The image of the illumination source 10 is created at the aperture stop 70 such that the source image underfills the aperture size. When underfilling the telecentric stop, the appropriate contrast of the imaged cells is generated so that they can be viewed clearly. The image of the illumination source is conjugate to the aperture stop.

As shown, the illumination source 10 and the detector 80 are configured to be positioned on the same side of the first surface 50 of the cell culture vessel 30. This configuration allows for the system 100 to operate in a bright field mode, thus backlighting the cells to be imaged. In a bright field mode, light from an illumination source enters an imaging objective lens assembly directly, and viewed objects absorb, change the phase of, or redirect some of the transmitted light such that the sample appears dark on a bright background. When operated in bright field mode, the system 100 allows for various aspects of cell culture health to be determined through image analysis of a bright field image, including, but not limited to, cell count, cell confluency, cell density, and cell migration tracking.

Figure 2:
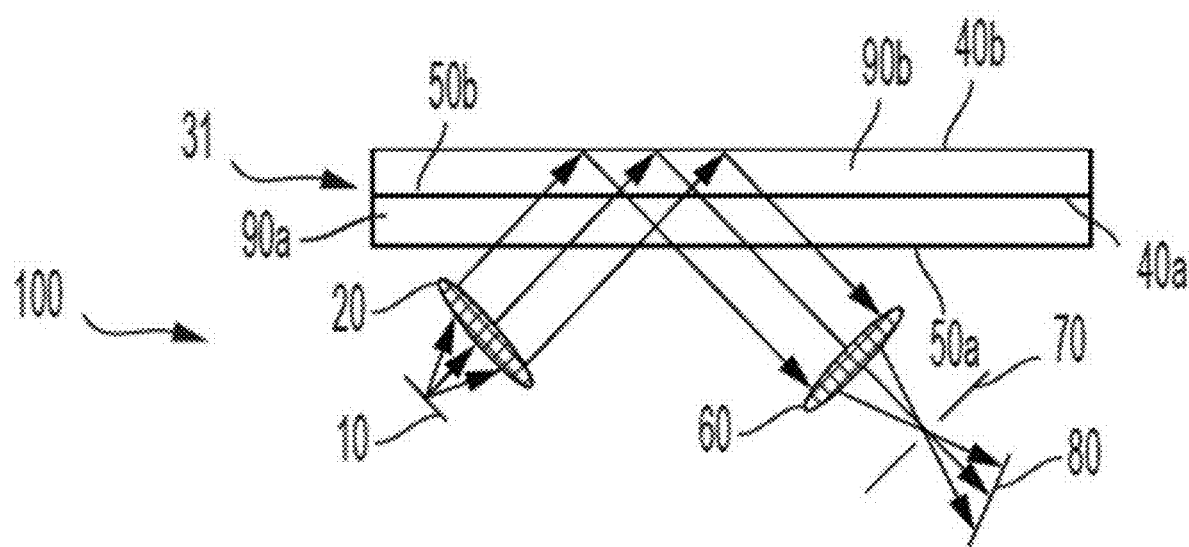
FIG. 2 schematically illustrates a detector/illumination source for multiple, stacked cell culture plates.

FIG. 2 illustrates an example of the optical imaging system 100, according to embodiments of this disclosure, for imaging cells in a multi-layered cell culture vessel 31, or in a stack of cell culture vessels. Components of the optical imaging system 100 correspond to those of like reference numerals in FIG. 1. The multi-layered cell culture vessel 31 includes a first cell culture vessel 90a having a first surface 50a and a second surface 40a on an opposite side of the first cell culture vessel 90a from the first surface 50a. The multi-layered cell culture vessel 31 further includes a second cell culture vessel 90b having a first surface 50b and a second surface 40b on an opposite side of the cell culture vessel 90b from the first surface 50b. The compact optical imaging system 100 operates similarly as described above with reference to the single-layered cell culture vessel as shown in FIG. 1. However, in the multi-layered cell culture vessel 31, the optical imaging system 100 can be arranged so that a light beam from the illumination source 10 can be redirected from the further (?) second surface 40b of the second cell culture vessel 90b toward the detection system.

According to embodiments of this disclosure, the cells to be imaged in a multi-layered cell culture vessel, such as the one shown in FIG. 2, for example, can be imaged using illumination that is redirected from a surface of a cell culture vessel other than the cell culture vessel containing the imaged cells. While the multi-layered cell culture vessel 31 of FIG. 2 only shows two cell culture vessels 90a, 90b, it is contemplated that embodiments of the compact optical imaging system can be used in multi-layered cell culture vessels having variety of numbers of layers or cell culture vessels. The light beam from the illumination source of the optical system can therefore be redirected by a surface of the cell culture vessel immediately above the cell culture vessel containing the cells to be imaged, or the light beam may be directed by a cell culture vessel that is two or more levels above the cell culture vessel containing the cells to be imaged. Further, the surface used to redirect the light beam from the illumination source can be a bottom surface (e.g., first surface 50b) of a cell culture vessel, or a top surface (e.g., second surface 40b) of a cell culture vessel.

In some embodiments each cell culture vessel can have a bottom surface upon which the cell culture rests. In such cases, the bottom surface of the next higher tray in the stack may act as the top for the vessel immediately below it and may be used to redirect light back into the cell culture. Alternatively, each cell culture vessel may have a cover which may serve as the surface from which the light is redirected into the cell culture. It is contemplated that each cell culture vessel (i.e. each layer in the stack) will contain only one cell culture.

Figure 3:
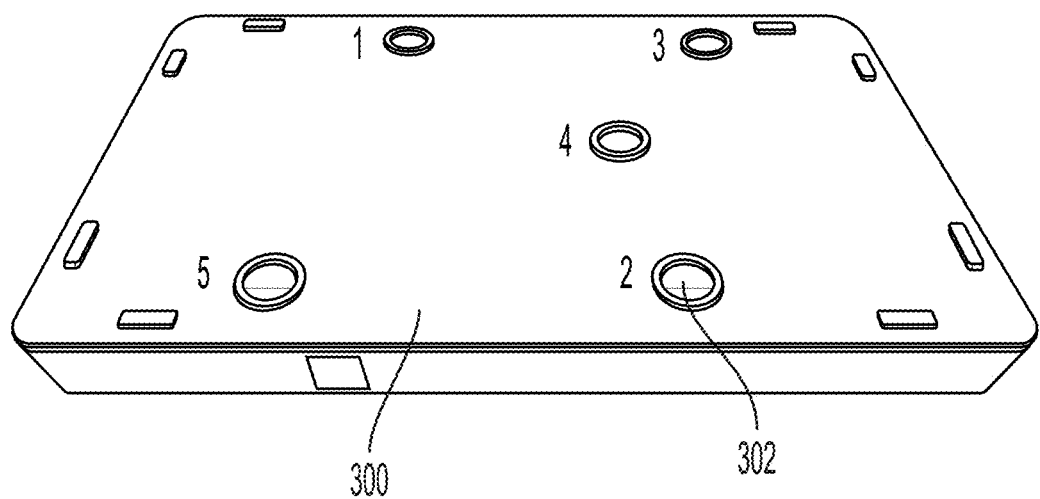
FIG. 3 is an illustration of a monitoring plate in accordance with one embodiment of the invention.

FIG. 3 shows an illustration of a monitoring plate 300 in accordance with an embodiment of the invention. The monitoring plate 300 shown is equipped with five optical imaging systems labeled 1-5. Each of the five apertures 302 shown in FIG. 3 services one optical imaging system 100, acting as an aperture for both transmission of the light source to the culture and collection of the image. Although the illustration of FIG. 3 shows five optical imaging systems 100, it would be realized by one of skill in the art that any number of optical imaging systems 100 can be used and that the multiple optical imaging systems 100 can be arranged in any way such as to provide coverage of the entire, or at least a majority of a cell culture vessel.

Figure 4:
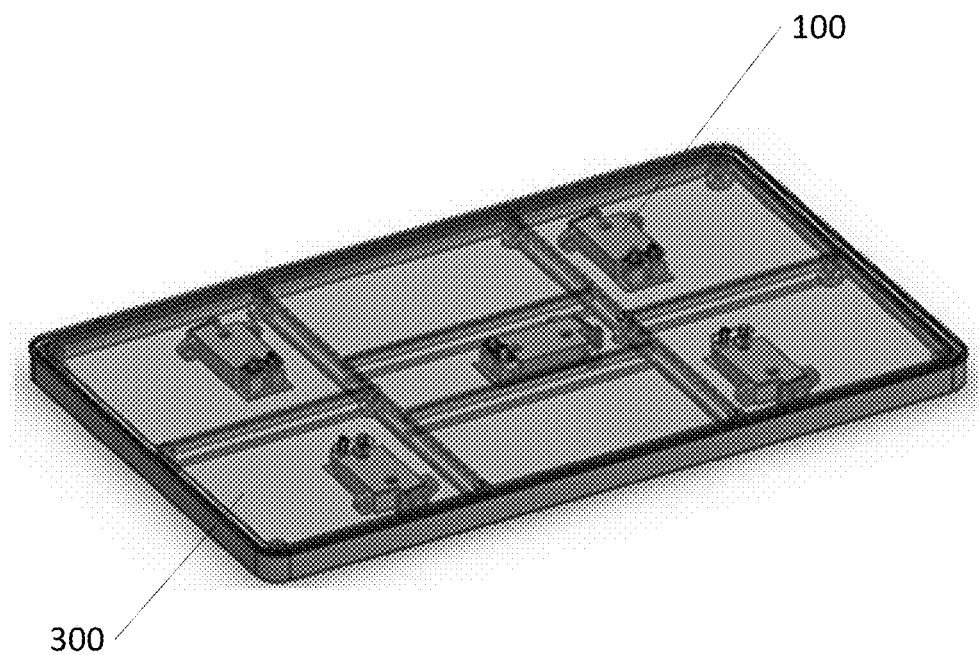
FIG. 4 is an illustration of the monitoring plate of FIG. 3 having the top removed to show the relative size and positioning of each optical imaging system with respect to the interior of the monitoring plate.

FIG. 4 shows monitoring plate 300 of FIG. 3 having the top removed to show the relative size and positioning of each optical imaging system 100 with respect to the interior of monitoring plate 300. Once again, the arrangement in number of optical imaging systems shown in FIG. 4 is exemplary in nature.

Figure 5B:
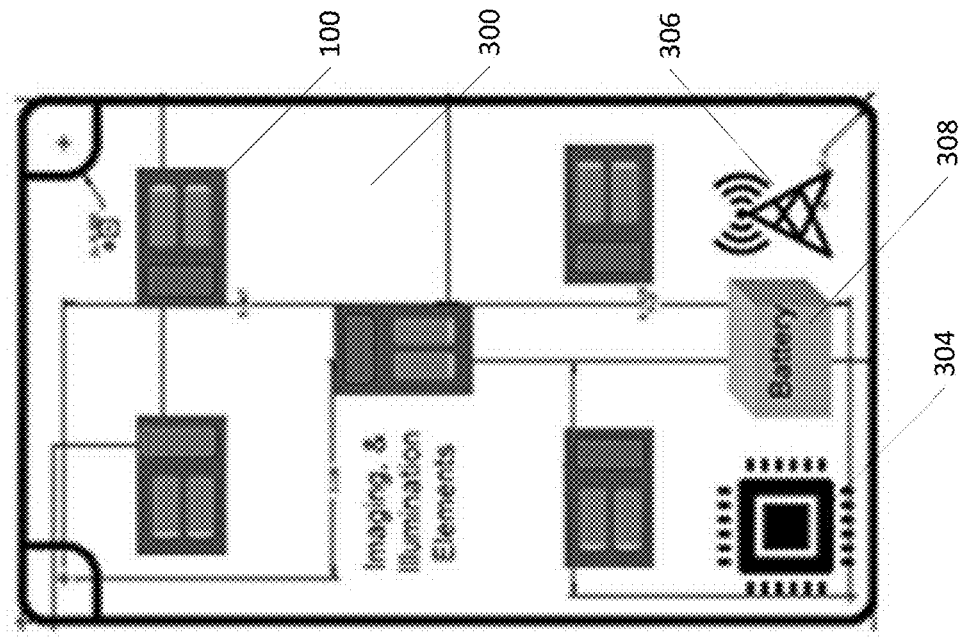
FIG. 5, View (A) is a logical block diagram showing components of the monitoring plate. View (B) shows one possible layout of the imaging portion of the components in the interior of the monitoring plate.
Figure 5A:
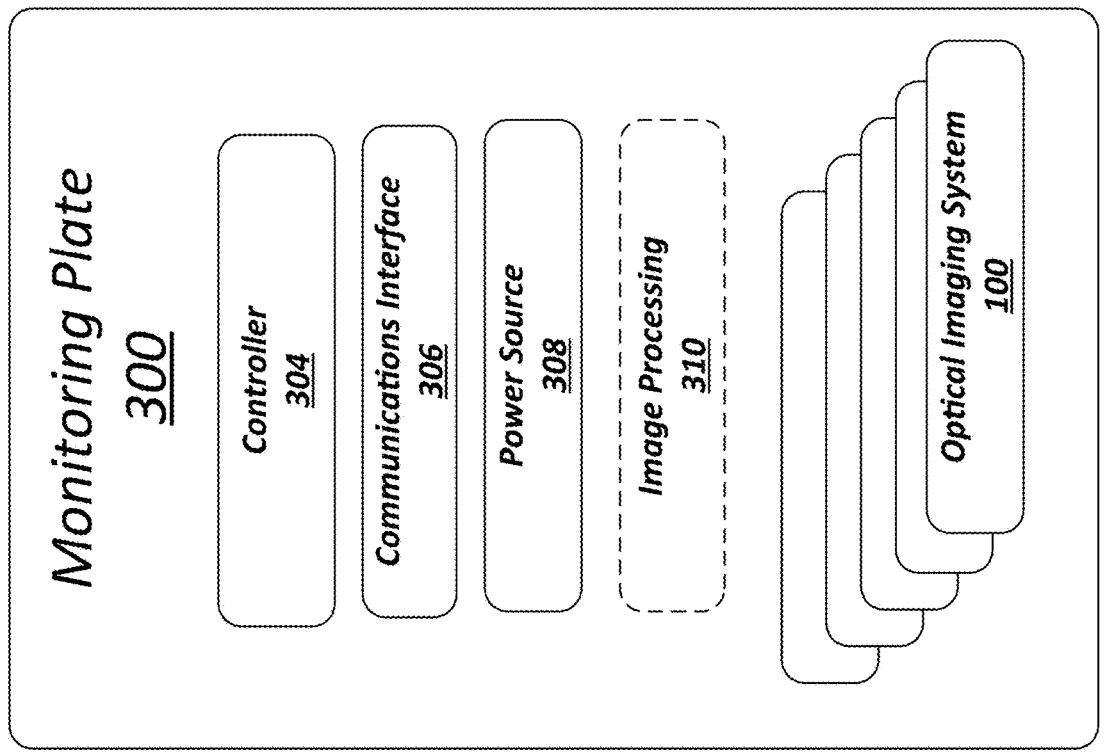

In addition to the multiple optical imaging systems 100, monitoring plate 300 may contain additional components, as shown in View (A) of FIG. 5. In addition to multiple optical imaging systems 100, monitoring plate 300 may include a controller component 304 for controlling the overall operation of the other components within monitoring plate 300. Monitoring plate 300 may be equipped with a communications interface 306 sending images collected by the multiple optical imaging systems 100 off unit for processing. Communications interface may be a wired connection or may be a wireless connection, for example, Wi-Fi or Bluetooth. Controller component 304 may receive commends via communication interface 306 to initiate imaging of the cell cultures. Monitoring plate 300 will also require a power source to power the controller 304, the communications interface 306 and the multiple optical imaging systems 100. Power source 308 may comprise a battery, a rechargeable battery or an external power source accessible via a power source interface. Monitoring plate 300 may also optionally include imaging processing component 310, which may optionally process the images collected by multiple imaging systems 100. In such a case, communications interface 306 would communicate the results of the image processing off unit in lieu of or in addition to transmitting the actual images off unit. Image processing component 310 may include one or more machine learning models trained to determine cell confluence based on images of cell cultures, or other means to determine cell confluence from images. View (B) of FIG. 5 shows one possible layout of the components shown in View (A) in the interior of monitoring plate 300.

Figure 6:
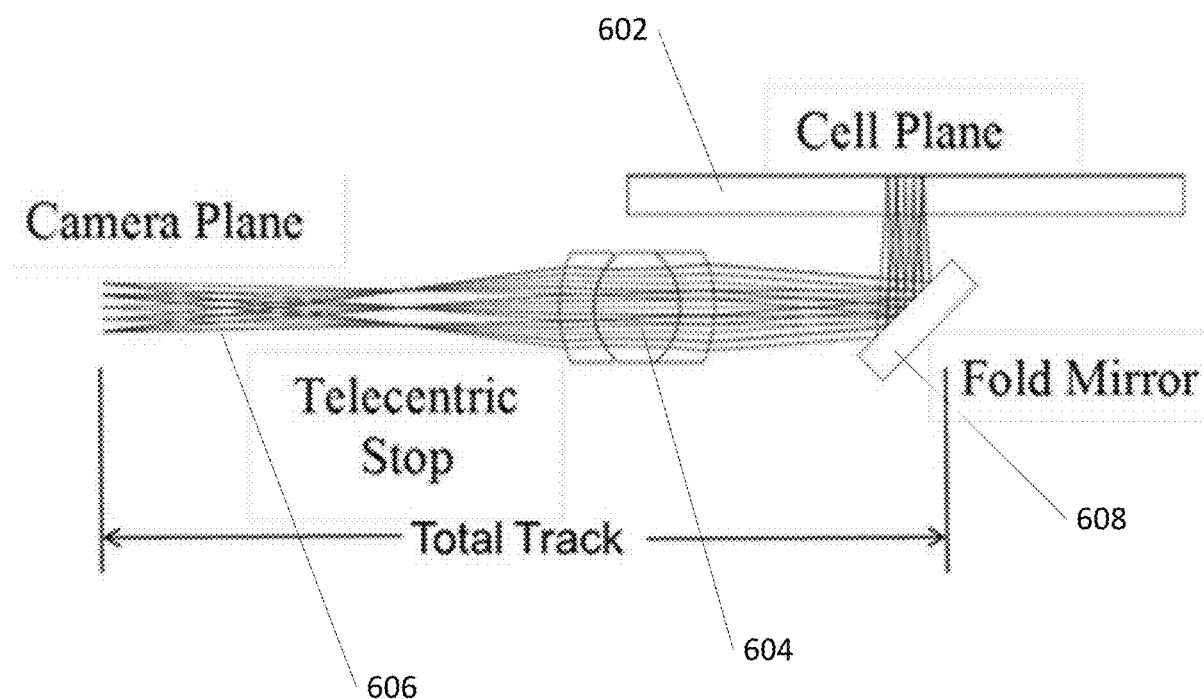
FIG. 6 is a schematic illustration of one embodiment of an optical path of a single optical imaging system suitable for use in the monitoring plate.

FIG. 6 shows one embodiment of a layout of the imaging portion of a single optical imaging system 100. The cells sit on the surface of the tray at the cell plane 602 and light from them is imaged by a lens 604. The image is formed at the camera plane 606 where the sensor resides. A telecentric aperture stop is placed at the rear focal point of the lens to ensure that the angular distribution of light across the images the same. Fold mirror 608 allows the optical imaging system 100 to be offset from and orthogonal to the aperture 302 in monitoring plate 300.

Figure 7:
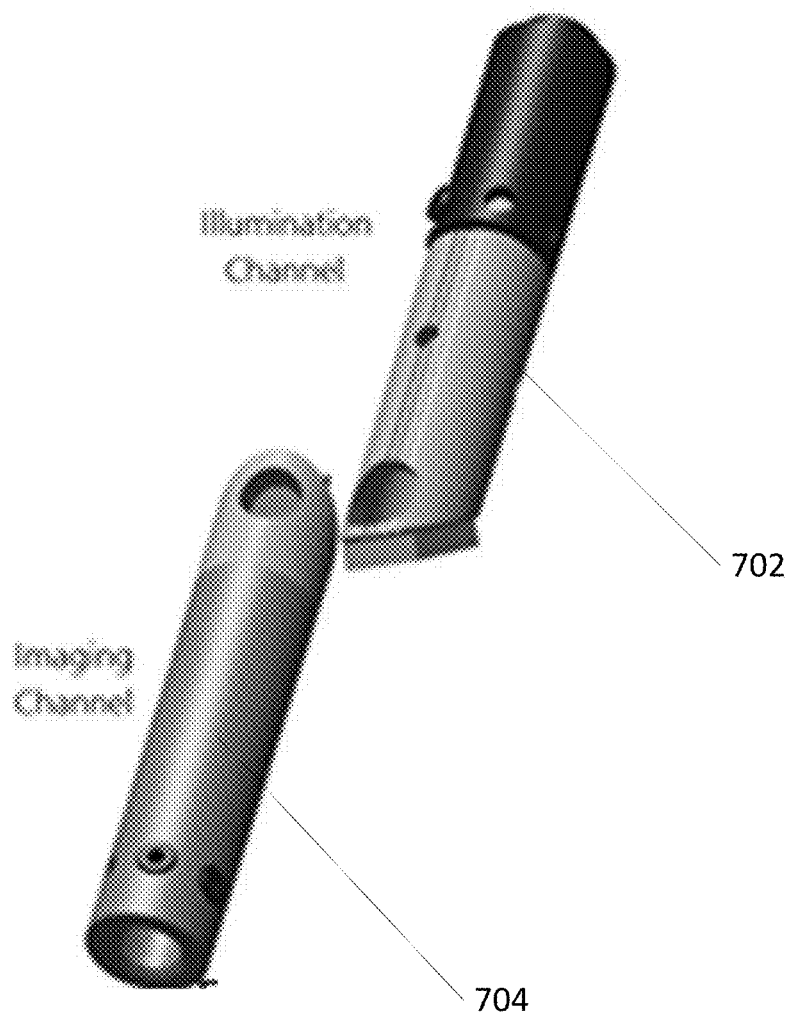
FIG. 7 is an illustration of one possible embodiment of a hardware configuration for containing the illumination component and the imaging component of an optical imaging system.
Figure 8:
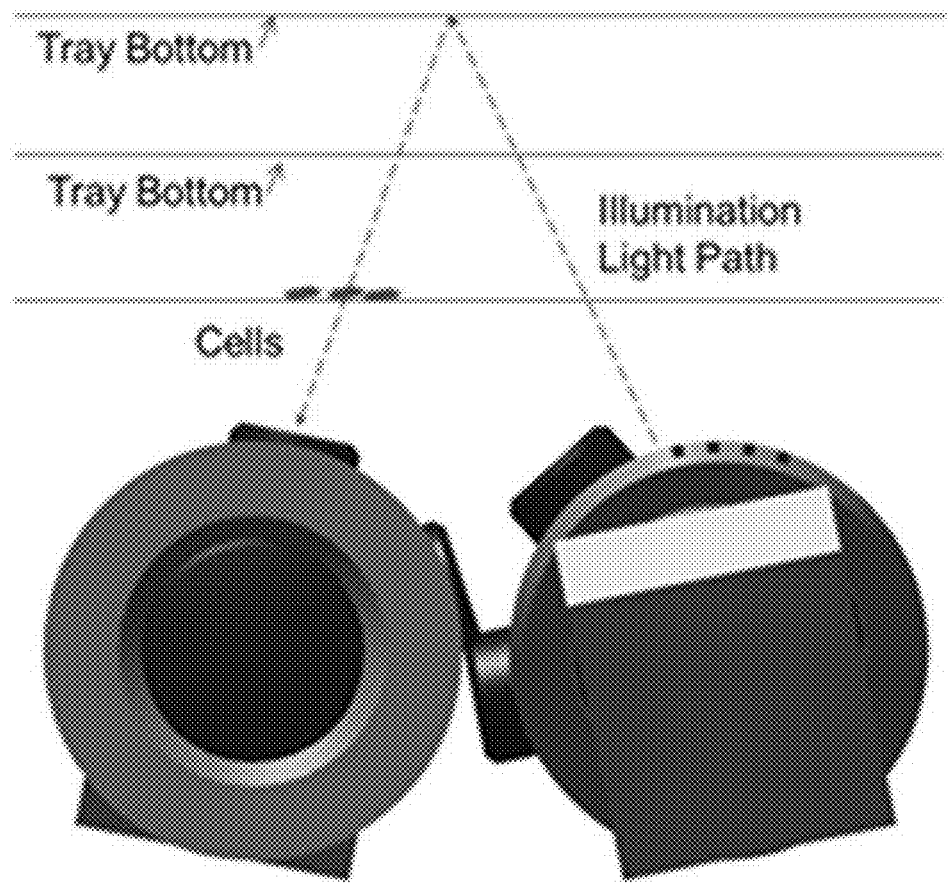
FIG. 8 is another view of the components of the optical imaging system of FIG. 7, showing their relative positions.

FIG. 7 shows one possible embodiment of a hardware configuration for containing the illumination component 702 and the imaging component 704. The illumination component 702 could be positioned above the imaging channel 704 at the expense of additional space in the stack of trays. However, FIG. 8 shows an embodiment which allows the illumination component 702 and the imaging component 704 to be kept in the same plane. In FIG. 8, the tubes containing the illumination component 702 and the imaging component 704 are rotated (or clocked) such that the illumination light passes through the cell tray and strikes another tray surface at an angle. This light then reflects off the tray surface and illuminates the cells from behind. Note that the plane that the cells are on is at an oblique angle to the optical axis of the imaging system. Illumination component 702 and imaging component 704 may be housed as a single optical imaging system 100 as shown in FIG. 4. It is contemplated that both illumination component 702 and imaging component 704 will both share aperture 302 defined in monitoring plate 300.

Figure 9:
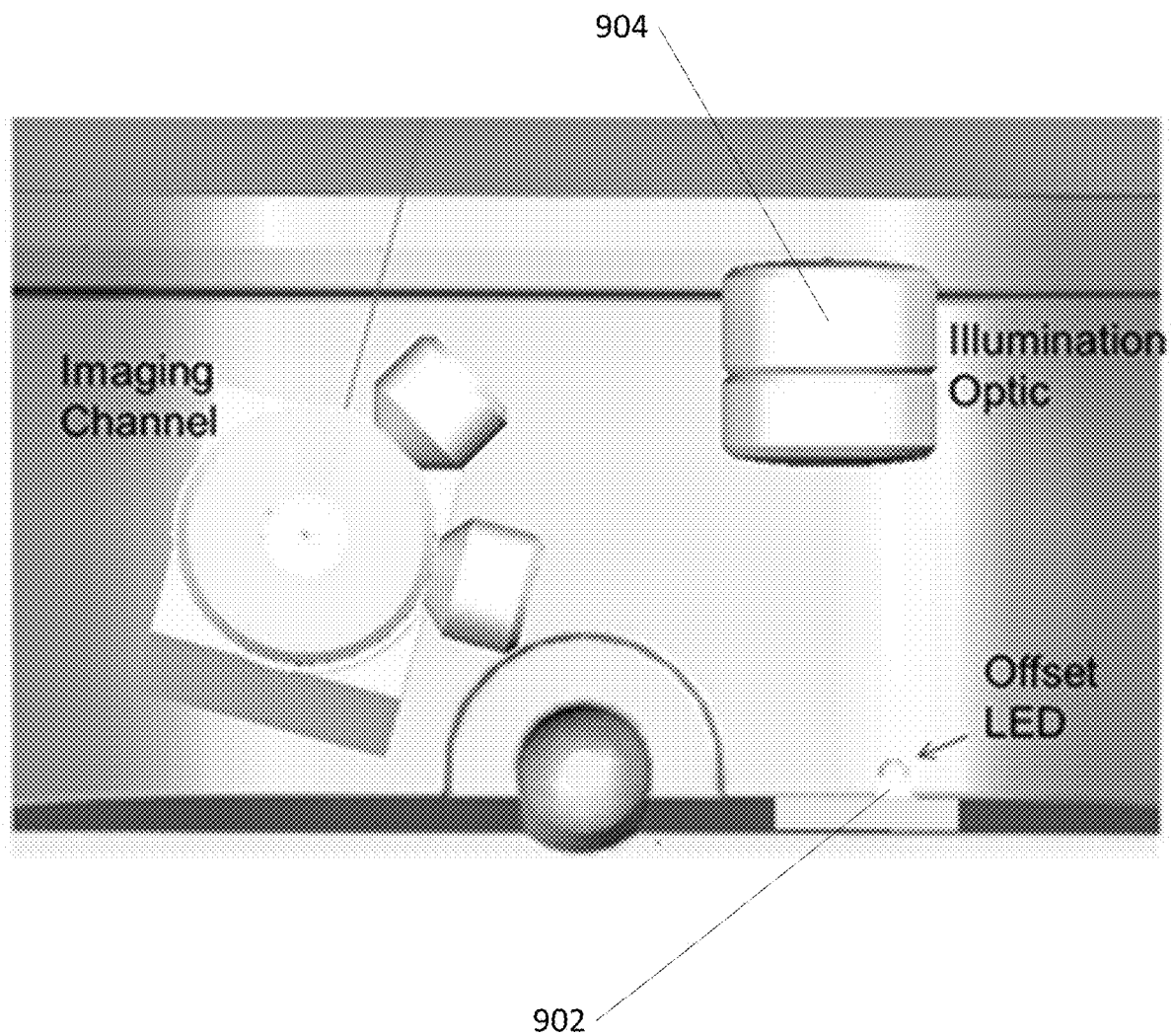
FIG. 9 shows an alternate embodiment for positioning components of the optical imaging system for providing off-angle illumination.

FIG. 9 shows an alternate embodiment for delivering the angled illumination. As shown in FIG. 9, the LED light source 902 is offset from the axis of the illumination optic 904. The amount of offset sets the illumination angle.

FIG. 10 shows several views of monitoring plate 300 showing one of the multiple optical imaging systems 100 positioned therein. View (A) of FIG. 10 shows a cutaway perspective view showing a single aperture 302 shared by illumination component 702 and imaging component 704. View (B) shows a side view of monitoring plate 300 showing that the arrangement of optical components previously describes allows the maintenance of the thin aspect ratio of monitoring plate 300. Also shown in View (B) is post 1002 protruding from the top surface of monitoring plate 300. Post 1002 allows the alignment of a cell culture vessel, for example, the cell culture vessel 1102 shown in View (A) of FIG. 11, with monitoring plate 300 and as such, with multiple optical imaging systems 100. View (C) shows a single aperture 302 defined in the service of monitoring plate 300 being shared by both imaging component 704 and illumination component 702.

Figure 11A:
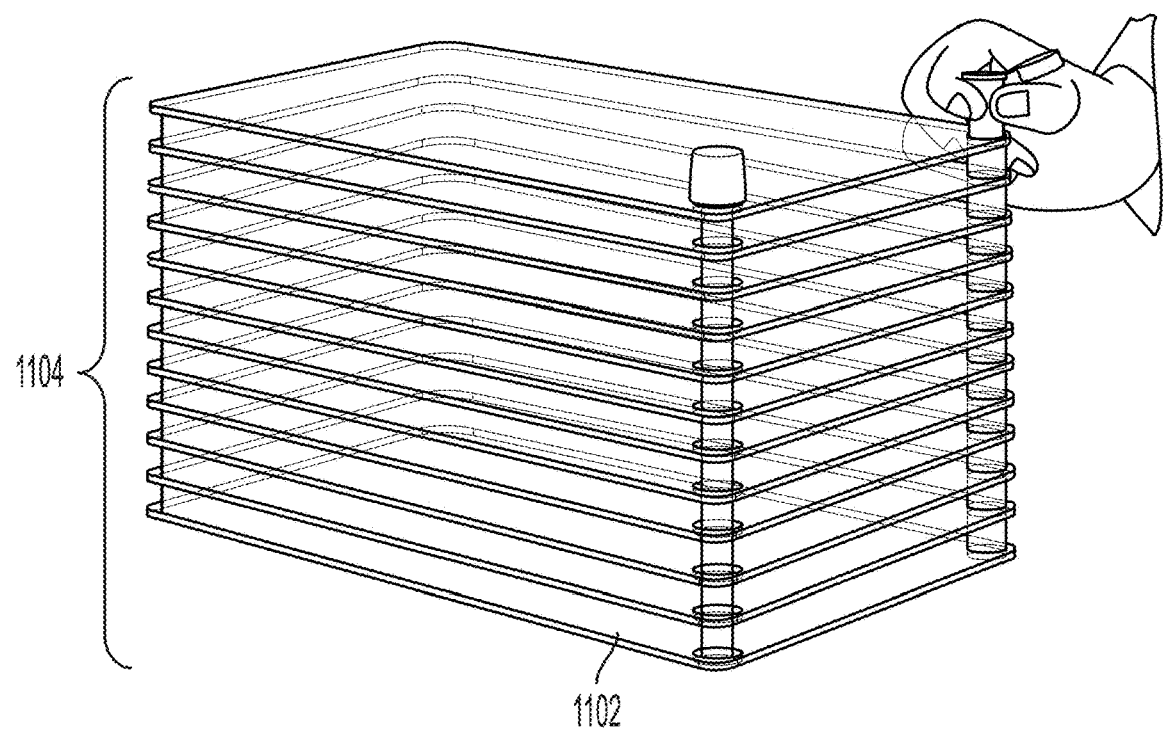
FIG. 11, Views (A,B) show two embodiments of commercially-available cell culture plates arranged in stacked configurations and suitable for use with the monitoring plate described herein.
Figure 11B:
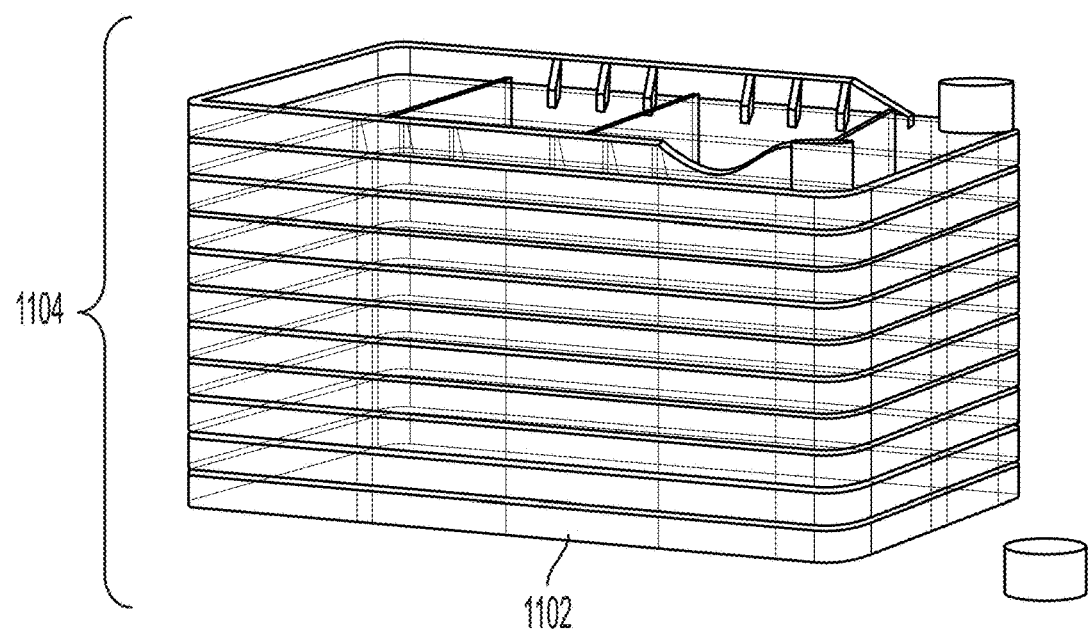
Figure 12:
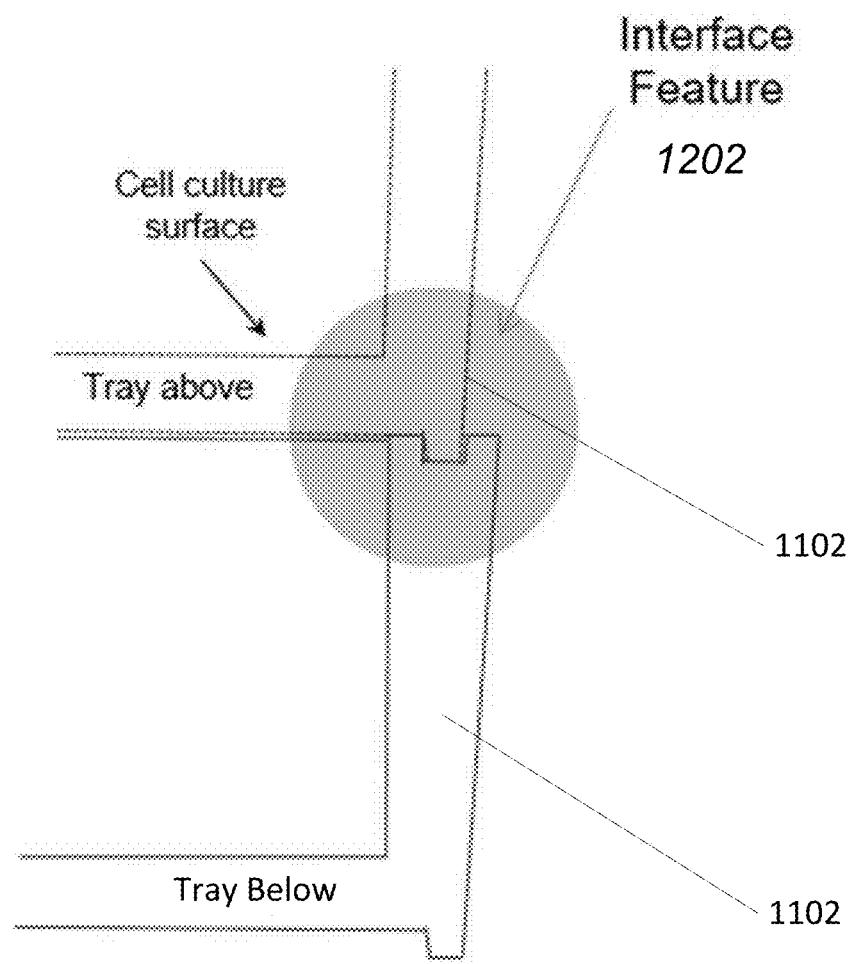
FIG. 12 shows one embodiment of an interface feature which allows for the stacking of the cell culture plates.
Figure 13:
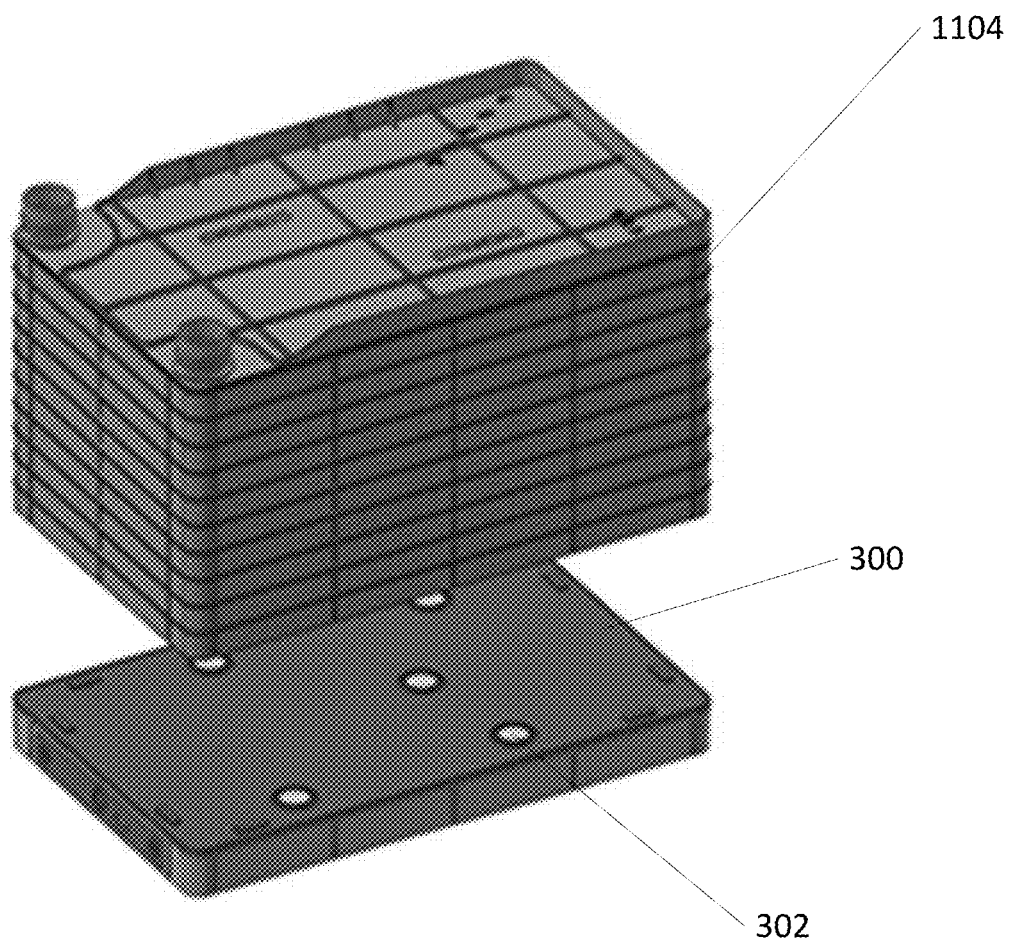
FIG. 13 is an illustration of stacked cell culture plates relative to monitoring plate.

FIG. 11, Views (A,B) are illustrations of several commercially-available cell culture vessels 1102 stacked one on top of another to form stack 1104, suitable for use with monitoring plate 300. FIG. 12 shows one embodiment of a method by which the trays 1102 may be aligned with each other by providing interface feature 1202. It should be noted that the interface feature 1202 shown in FIG. 12 is exemplary only and that any means of aligning the cell culture vessels 1102 one on top of the other is contemplated to be within the scope of the invention. FIG. 13 shows a stack of cell culture vessels 1104 about to be placed on monitoring plate 304 imaging.

In one embodiment of the invention, it is contemplated that only the bottom cell culture vessel 1102 of stack 1104 will be imaged. In such a case, the optical parameters of each optical imaging system 100, for example, the focal length of imaging component 704, may be preset such as to be focused only on the bottom most layer of stack 1104. Thereafter, it may be assumed that upper layers of stack 1104 will contain cultures having similar characteristics to the culture in the bottom most layer. In such a case, the results for the upper layers of stack 1104 may be interpolated based on the measurement of the bottom most layer.

In alternate embodiments, is contemplated that optical imaging systems 100 will be able to refocus such as to be focused on upper layers of stack 1104. In such a case, the optical parameters, including the focal length of imaging component 704 may need to be adjusted to be focused on a particular layer within stack 104. The components comprising imaging component 704 and illumination component 702 may be moved via mechanical means, for example, servos or MEMS components. In alternate embodiments, the components may be dynamically configurable to change their characteristics in a non-mechanical manner. In addition, to image multiple layers in stack 1104 will be necessary that illumination component be capable of illuminating specific layers, which means that the source of illumination must be capable of illuminating the layers through one or more layers of cultures below the layer being image. In such cases, it is contemplated that illumination source may be, for example, a laser's light source, a infrared light source, or a wide spectrum light source having a high-intensity.

As one non-limiting example of the invention, the optical imaging systems 100 may be configured as described in FIG. 1 or FIG. 2 such that the direction of the light beam emitted by the illumination component 702 enters a cell culture vessel of a cell culture layer 1102 positioned above monitoring plate 300 at an angle oblique to the surface of the cell culture layer 1102. Similarly, the imaging component 704 of the optical imaging system 100 is positioned at an oblique angle relative to the direction of the light beam being received by the optical sensor from the cell culture layer 1102. The direction of the light beam is also at an angle that is oblique to the surface of the cell culture layer 1102 as it passes through the area of the cell culture layer 1102 where the cells being imaged are located. Because the light passes through the surface of the cell culture vessel at an oblique angle, the light beam is also at an oblique angle relative to the cells adhered to that surface. This will result in a focus shift across the field of view if the image sensor is perpendicular to the light beam. Thus, the image sensor can be positioned at an oblique angle relative to the light beam so that the cells can be imaging in focus across the field of view, in accordance with the Scheimpflug principle. In operation of the optical imaging system 100, a light beam is emitted from the illumination component 702 positioned in monitoring plate 300 in the direction of the cell culture layer 1102 positioned above monitoring plate 300, wherein a first surface of the cell culture layer 1102 contains live cells to be imaged. The light beam travels into and through the cell culture layer 1102, contacts the bottom surface of the cell culture layer 1102 positioned directly above the cell culture layer 1102 being imaged, and is redirected at an angle in the direction of the image sensor positioned in the monitoring plate 300. After being redirected, the light passes through cells on the first surface of the cell culture layer 1102 and is focused to the image sensor.

Figure 14:
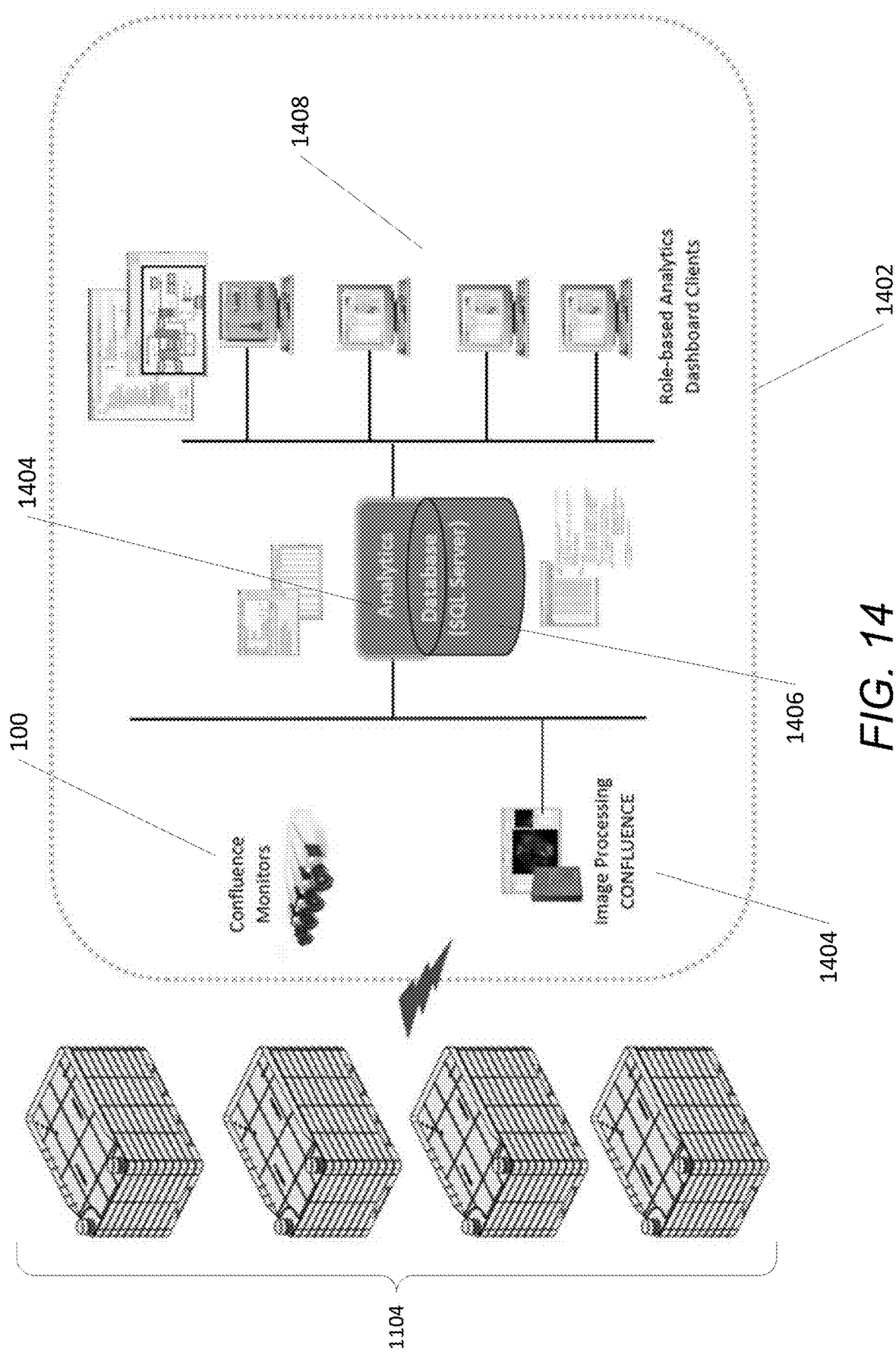
FIG. 14 is a logical diagram of a system for applying analytics to the images captured by the one or more monitoring plates to determine cell confluence and other characteristics of the cultures.

The images obtained from multiple imaging systems 100 may be processed to determine the confluence of the cell cultures contained in cell culture layers 1102. FIG. 14 shows a system for making the determination of the cell confluence. Multiple images from multiple stacks 1104 of cell cultures to be received by system 1402. Analytics component 1402 may analyze the images using analytics 1404 to approximate a value for the cell confluence exhibited by each layer 1102 in stacks 1104. Analytics 1404 may comprise, for example, one or more machine learning databases trained to approximate confluence. In alternative embodiments, other forms of analytics may be used. Analytics 1404 may utilize database 1406 in support of the effort to analyze the images. Database 1406 may contain, for example, the machine learning models used to analyze the images. Results of the analysis from analytics 1404 may be output on one or more dashboard clients 1408 which may present the results in a variety of different ways.

Figure 15:
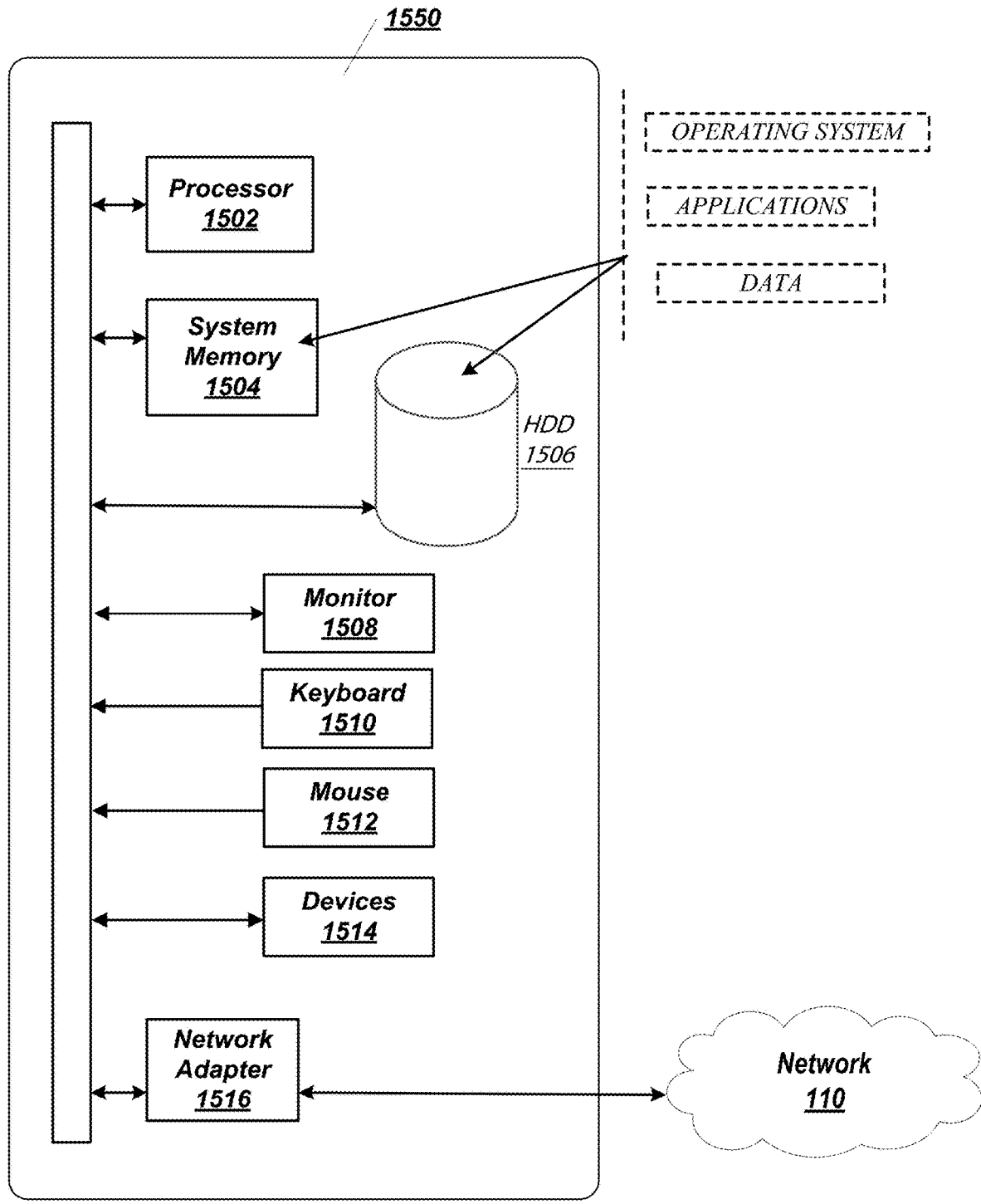
FIG. 15 shows a computing architecture suitable for supporting the functions of the connected ecosystem for the laboratory environment as described herein.

The analytics component 1402 may be embodied as hardware accompanied by a processor executing instructions from a non-volatile, computer-readable medium. A computing architecture suitable for use in support of the systems and apparatuses is shown in FIG. 15, which illustrates an embodiment of an exemplary computing architecture 1500 suitable for implementing the various embodiments as previously described. In one embodiment, the computing architecture 1500 may, in whole or in part, comprise or be implemented as part of an electronic device, such as a computer, smartphone or tablet computing device 1550. The embodiments are not limited in this context.

As used in this application, the terms "system" and "component" are intended to refer to a computer-related entity, either hardware, a combination of hardware and software, software, or software in execution, examples of which are provided by the exemplary computing architecture 1500. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 1500 includes various common computing elements, such as one or more processors, multi-core processors, co-processors, memory units, chip-sets, controllers, peripherals, interfaces, oscillators, timing devices, video cards, audio cards, multimedia input/output (I/O) components, power supplies, and so forth, all of which are able to communicate as necessary using appropriate connections. The embodiments, however, are not limited to implementation by the computing architecture 1500.

As shown in FIG. 15, the computing architecture 1500 comprises computer 1550 comprising a processor 1502, and a system memory 1504. The processor 1502 can be any of various commercially available processors. Dual microprocessors, multi-core processors, and other multi-processor architectures may also be employed as processor 1502.

An interface is provided for system components including, but not limited to, the system memory 1504 to the processing unit 1502. The interface can be any of several types of bus structure that may further interconnect to a memory bus (with or without a memory controller), a peripheral bus, and a local bus using any of a variety of commercially available bus architectures. Interface adapters may connect to the system bus 1206 via a slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The computing architecture 1500 may comprise a non-volatile, computer-readable storage medium, such as a hard disk drive (HDD) or solid state drive to store logic. Examples of a computer-readable storage medium may include any tangible media capable of storing electronic data, including volatile memory or non-volatile memory, removable or non-removable memory, erasable or non-erasable memory, writeable or re-writeable memory, and so forth. Examples of logic may include executable computer program instructions implemented using any suitable type of code, such as source code, compiled code, interpreted code, executable code, static code, dynamic code, object-oriented code, visual code, and the like. Embodiments may also be at least partly implemented as instructions contained in or on a non-transitory computer-readable medium, which may be read and executed by one or more processors to enable performance of the operations described herein.

The system memory 1504 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. A basic input/output system (BIOS) can be stored in a non-volatile portion of system memory 1504.

The drives and associated computer-readable media provide volatile and/or nonvolatile storage of an operating system 1520, applications 1522, and related data and data structures 1524. Applications 1522 may be in the form of software comprising computer-executable instructions. In one embodiment, the one or more applications 1522 and data 1524 may comprise, for example, the analytics component 1402 described above and used to analyze images received from one or more monitoring plates 300.

A user can enter commands and information into the computer 1550 through one or more wire/wireless input devices, for example, a keyboard 1510 and a pointing device, such as a mouse 1512. Other devices 1514 may include, for example, monitoring plate 300, or a smart incubator. Other types of user input devices 1514 may include, for example, microphones, infra-red (IR) remote controls, radio-frequency (RF) remote controls, game pads, electronic pencils, card readers, dongles, finger print readers, gloves, graphics tablets, joysticks, keyboards, retina readers, touch screens (e.g., capacitive, resistive, etc.), trackballs, trackpads, sensors, projectors, lasers scanners and the like. These and other input and output devices are often connected to computer 850 via various means, including serial ports, USB connections, wired network connections, Wi-Fi connections, Bluetooth connections, etc.

A monitor 1508 or other type of display device may be used to provide video output 222 to a user. The monitor 1508 may be internal or external to the computer 1550. Monitor 1508 may act as both a display device and as an input device, as in the case of a touch-screen display commonly found on smartphones and tablet computing devices. In addition to the monitor 1508, a computer typically includes other peripheral output devices, such as speakers, printers, and so forth which may be used to provide audio outputs 224.

The computer 1550 may operate in a networked environment using logical connections via wire and/or wireless communications to one or more remote, networked computers, such as monitoring plates 300. The networked computer can be a workstation, a server computer, a router, a personal computer, portable computer, microprocessor-based entertainment appliance, a peer device or other common network node, and typically includes many or all of the elements described relative to the computer 1550. The logical connection depicted includes connectivity to a local area network (LAN) or wide area network (WAN) 110. Such LAN and WAN networking environments are commonplace in offices and companies, and facilitate enterprise-wide computer networks, such as intranets, all of which may connect to a global communications network, for example, the Internet. Computer 1550 may be connected to the LAN/WAN 110 via a wired or wireless communication network interface or adaptor 1516. Network adapter 1516 can facilitate wired or wireless communications to the LAN/WAN 110, which may also include a wireless access point disposed thereon for communicating with the wireless functionality of the network adaptor 1516.

A monitoring plate 300 having multiple integrated optical imaging systems 100 for imaging one or more layers of cull culture vessels 1102 has been described herein. In addition, an analytics component 1402 for analyzing images received from one or more monitoring plates 300 and for estimating the cell confluence of cell cultures contained in one or more layers of cull culture vessels 1102, as well as the computing architecture 1500 sufficient to support the analytics component 1402, have been described herein. Exemplary physical and logical components and arrangements of components have been used in the description of the monitoring plate 300 and analytics component 1402, however, as will be realized by one of skill in the art, many different arrangements of the physical and logical components, or substitutions therefor, may be used without deviating from the intended scope of the invention. For example, different configurations of illumination component 702 and imaging component 704 are within the scope of the invention.

What is claimed is:

1. An apparatus comprising:
   a housing having a flat top surface;
   one or more apertures disposed in the flat top surface;
   one or more optical imaging systems disposed within the housing and configured to image a culture in a cell culture vessel placed on the flat top surface of the housing, the one or more optical imaging systems each comprising an imaging component and an illumination component that share an aperture of the one or more apertures disposed in the flat top surface;
   wherein the illumination component is configured to direct light at an oblique angle to a surface above the culture in the cell culture vessel such that the light is reflected off of the surface such as to illuminate the culture from a side opposite the imaging component, wherein the surface reflecting the light is a bottom surface of a second cell culture vessel stacked on top of the cell culture vessel placed on the flat top surface of the housing; and
   wherein the illumination component is configured to vary the oblique angle such as to illuminate cultures located in cell culture vessels stacked on the cell culture vessel placed directly on the top surface of the housing.

2. The apparatus of claim 1, the imaging component being disposed in the housing offset from one of the apertures in the top surface of the housing, further comprising:
   a mirror located directly underneath the aperture and angled to direct light from the culture to the imaging component.

3. The apparatus of claim 2, the imaging component having a focal length fixed to image the culture in the cell culture vessel placed directly on the top surface of the housing.

4. The apparatus of claim 2, the imaging component having a movable focal length which may be adjusted to image cultures located in cell culture vessels stacked on the cell culture vessel placed directly on the top surface of the housing.

5. The apparatus of claim 1, further comprising:
a communications interface;
a controller; and
a power source for powering communications interface, the controller, and the one or more optical imaging systems.

6. The apparatus of claim 5, the controller receiving commands via the communication interface to image cultures located in one or more cell culture vessels stacked on the top surface of the housing.

7. The apparatus of claim 6, the controller transmitting images from the one or more optical imaging systems via the communications interface.

8. The apparatus of claim 5, further comprising:
an image processing component for processing of images collected from the one or more optical imaging systems.

9. The apparatus of claim 8, the imaging processing component analyzing images collected from the one or more optical imaging systems to determine confluence of cell cultures located in one or more cell culture vessels stacked on the top surface of the housing.

10. The apparatus of claim 9, the imaging processing component comprising one or more machine learning models trained to determine cell confluence from images.

11. The apparatus of claim 9, the imaging process component configured to transmit the results of the image analysis via the communications interface.

12. A method for determining cell confluence of a cell culture in a cell culture vessel comprising:
providing one or more optical imaging systems, each optical imaging system comprising an imaging component and illumination component within a housing disposed below the cell culture vessel, wherein the illumination component is configured to direct light at an oblique angle through cell culture in the cell culture vessel such that the light is reflected off of a surface above the cell culture vessel such as to illuminate the cell culture from a side opposite the imaging component, wherein the surface reflecting the light is a bottom surface of a second cell culture vessel stacked on top of the cell culture vessel;
directing light from the illumination component at an oblique angle to a reflective surface above the cell culture such that the cell culture is illuminated from a side opposite the imaging component;
capturing an image of the illuminated cell culture with the imaging component; and
varying the oblique angle of the illumination component so as to illuminate cultures located in cell culture vessels stacked on the cell culture vessel placed directly on the top surface of the housing.

13. The method of claim 12, further comprising collecting images of the cell culture from one or more of the optical imaging systems.

14. The method of claim 13, further comprising transmitting the collected image via a communications interface.

15. The method of claim 13, further comprising analyzing the collected images using an image processing component, the image processing component configured to detect cell confluence in the cell culture.

16. The method of claim 15, further comprising transmitting the results of the image analysis via the communications interface.

* * * * *